United States Patent [19]
Hattori et al.

[11] Patent Number: 5,504,065
[45] Date of Patent: Apr. 2, 1996

[54] AGENT FOR TREATING OR PREVENTING AIDS USING HUMAN URINE TRYPSIN INHIBITOR

[75] Inventors: Toshio Hattori; Kiyoshi Takatsuki, both of Kumamoto; Yoshikazu Yuki, Kobe, all of Japan

[73] Assignee: JCR Pharmaceuticals Co., Ltd., Hyogo, Japan

[21] Appl. No.: 261,746

[22] Filed: Jun. 17, 1994

Related U.S. Application Data

[63] Continuation of Ser. No. 158,819, Nov. 26, 1993, abandoned, which is a continuation of Ser. No. 960,199, Oct. 9, 1992, abandoned, which is a continuation of Ser. No. 831,080, Feb. 5, 1992, abandoned, which is a continuation of Ser. No. 436,830, Nov. 15, 1989, abandoned.

[30] Foreign Application Priority Data

Nov. 28, 1988 [JP] Japan .................................. 63-302058

[51] Int. Cl.⁶ ......................... A61K 38/14; A61K 38/57
[52] U.S. Cl. .............................. 514/8; 530/395; 530/397; 530/834
[58] Field of Search .................. 514/8; 500/395, 500/397, 834

[56] References Cited

U.S. PATENT DOCUMENTS 4,780,209  10/1988  Yuki et al. ............................... 210/635

OTHER PUBLICATIONS

Proksch et al, J. Lab. Clin. Med. pp. 491–499 (1972).

*Primary Examiner*—Howard E. Schain
*Attorney, Agent, or Firm*—Burgess, Ryan and Wayne

[57] ABSTRACT

Human urine trypsin inhibitor is provided as an agent for treating acquired immunodeficiency syndrome (AIDS), preventing the infection with AIDS or preventing the onset of AIDS after such infection. It can be administered intravenously for the treatment and externally for the prevention.

2 Claims, 1 Drawing Sheet

AGENT FOR TREATING OR PREVENTING AIDS USING HUMAN URINE TRYPSIN INHIBITOR

This application is a continuation of application Ser. No. 08/158,819, filed Nov. 26, 1993, now abandoned, which is a continuation of application Ser. No. 07/960,199, filed Oct. 9, 1992, now abandoned, which is a continuation of application Ser. No. 831,080, filed Feb. 5, 1992, now abandoned, which is a continuation of application Ser. No. 436,830, filed Nov. 15, 1989, now abandoned.

BACKGROUND OF THE INVENTION

1. Field of the Invention

This invention relates to an agent for treating acquired immunodeficiency syndrome (AIDS), preventing AIDS virus infection and preventing the onset of AIDS after such infection.

2. Description of the Prior Art

AIDS is now a focus of worldwide attention as a disease induced by human immunodeficiency virus (HIV, or AIDS virus) and characterized by bad prognosis.

When infected with HIV, helper T cells, among others, are destroyed. Insufficiency of immunological competence thus results and this leads to such clinical features as serious opportunistic infection, carinii pneumonia, Kaposi sarcoma and AIDS-related encephalopathy. The disease is highly fatal.

HIV infection-associated states or illnesses include a symptomatic carrier state, progressive or persistent generalized lymphoadenophathy (PGL), lymphoadenophathy syndrome (LAD), AIDS-related complex (ARC) and AIDS. No effective therapy for AIDS has been established as yet. The only agent known to be effective is 3'-azidothymidine that has been shown to have obvious life-prolonging effect in patients with AIDS who are suffering from carinii pneumonia.

AZT is an HIV reverse transcriptase inhibitor and this effect brings about improvements in clinical symptoms and neurologic symptoms and temporary restoration of certain immune functions [H. Mitsuya et al.; Nature, 325, 773 (1987)]. Therefore, AZT is highly toxic to bone marrow and about 50% of patients treated with AZT require blood transfusion.

No virucidal agent capable of specifically killing HIV without causing any serious adverse reactions in humans has not been discovered as yet.

Reverse transcriptase inhibitors, such as AZT, cannot be considered to be potent therapeutic agents since they produce adverse effects and are effective only in the postponing of death.

Accordingly, it is an object of the invention to provide an agent for treating AIDS and preventing HIV infection or the onset of AIDS after HIV infection.

The present inventors made investigations into the interactions between AIDS virus and T cells or, in other words, the sites of infection.

AIDS virus has an envelope glycoprotein (gp-120). Investigations have shown that gp-120 has a T cell receptor (CD-4)-binding site within the amino acid sequence from the 397th (from the N terminus of gp-120) to the 439th amino acid thereof [A. L. Lawrence et al.: Cell, 50, 975 (1987)].

According to more recent findings, the 24 amino acids (called epitope $\beta$) from the 308th (from the N terminus) to the 332th amino acid of gp-120 plays an important role in HIV infection [T. J. Palker: Proc. Natl. Acad. Sci. U.S.A., 85, 1932 (1988); S. Matsushita: J. Virol., 62 (6), 2107 (1988)]. That is to say, researchers, inclusive of the present inventors, have revealed that monoclonal antibodies to epitope $\beta$ of gp-120 can inhibit HIV infection.

Accordingly, the present inventors searched for proteins having an amino acid sequence homologous to epitope $\beta$ using the National Biomedical Research Foundation data base. As a result, 90 proteins were listed, 11 of which were proteases or protease inhibitors.

Among them, inter-$\alpha$-trypsin inhibitors (ITIs), not only human ITI but also ITIs derived from various animals, showed that highest degree of homology to epitope $\beta$.

The arginine residue (Arg) in the homologous region was the protease activity inhibiting site of ITIs.

While epitope $\beta$ is the variable region of gp-120, the amino acid sequence comprising several amino acids with Arg as the central figure was preserved in various HIV-1 strains. Therefore, the present inventors synthesized a peptide having 33 amino acids in its amino acid sequence, including the 54 amino acids of epitope $\beta$ and evaluated it for trypsin activity inhibition by it. As a result, it was found that said peptide could inhibit trypsin activity by 30% when BOC-Phe-Ser-Arg-MCA was used as a synthetic substrate.

It was thus suggested that epitope $\beta$ might have protease inhibitor activity or be a very good substrate for protease.

Human ITI is a glycoprotein occurring in human serum. It is a single-chain glycoprotein having an apparent molecular weight of about 180,000 as determined by SDS-PAGE (sodium dodecyl sulfate-polyacrylamide gel electrophoresis) and a carbohydrate content of about 8%. It is stable to acids and heat.

On the other hand, human urine trypsin inhibitor (hereinafter referred to as "UTI") purified from human urine is a single-chain glycoprotein having an apparent molecular weight of about 45,000 as determined by SDS-PAGE. It is stable to heat and acids.

Since both have the identical amino acid sequence on the N-terminal side, the ITI is presumably a precursor to UTI ("Proteinase Inhibitors", edited by A. J. Barrett et al., pages 389–398, Elsevier, 1986). UTI has two kunitz type domains closely resembling each other within its molecule. Nothing is known at all about what action, if any, said ITI and/or UTI can exert upon AIDS virus, however.

In Japan, human UTI, also called urinastatin by generic name, is currently in wide clinical use as a drug for the treatment of acute pancreatitis and acute ventricular failure (hemorrhagic shock, septic shock, traumatic shock, burn shock).

Since it is a glycoprotein derived from human urine, UTI is a very highly safe drug, scarcely presenting antigenicity, toxicity and other problems to humans.

For these reasons, the present inventors performed an in vitro infection neutralization test to see whether UTI might be actually effective against HIV infection.

The inhibition of HIV infection was assessed by the syncytium formation inhibition method, namely using, as an index, the syncytium formation inhibition in a mixed cell culture system containing LAV-1-infected CCRF-CEM cells and AIDS infection-free MOLT-4 clone 8 cells.

In this way, UTI was found to inhibit, in a serum-free culture system, syncytium formation strongly at concentrations not lower than 300 μM, moderately at a concentration of 100 μM, and weakly at 30 μM. Soybean trypsin inhibitor (SBTI) was also tested by the above method since epitope β shows homology, though weak, to the active site of SBTI. SBTI inhibited syncytium formation in a concentration-dependent manner at concentrations of 300 μM to 3 mM, although its inhibitory activity was weaker than that of UTI.

On the contrary, aprotinin, which is a bovine lung-derived trypsin inhibitor, did not inhibit syncytium formation.

SBTI and aprotinin, which are heterologous proteins other than human-derived proteins, offer the antigenicity problem when they are repeatedly administered to humans. On the other hand, UTI can be considered to be an agent having very low toxicity. In fact, in acute toxicity testing in mice, rats and dogs, an intravenous dose of $150 \times 10^4$ IU/kg body weight (i.e. about 600 mg/kg body weight) gave no deaths.

In subacute toxicity testing, where a maximum daily dose of $60 \times 10^4$ IU/kg body weight (i.e. about 240 mg/kg body weight) was intravenously administered to rats and a maximum daily dose of $30 \times 10^4$ IU/kg body weight (i.e. about 120 mg/kg body weight) to dogs for consecutive 4 weeks, no serious adverse reactions were noted.

SUMMARY OF THE INVENTION

The present invention, that has been completed on the above findings, provides a therapeutic or prophylactic composition for the treatment of AIDS, the prevention of AIDS virus (HIV) infection or the prevention of the onset of AIDS after such infection which contains human urine trypsin inhibitor (UTI).

DETAILED DESCRIPTION OF THE INVENTION

Figure 1:
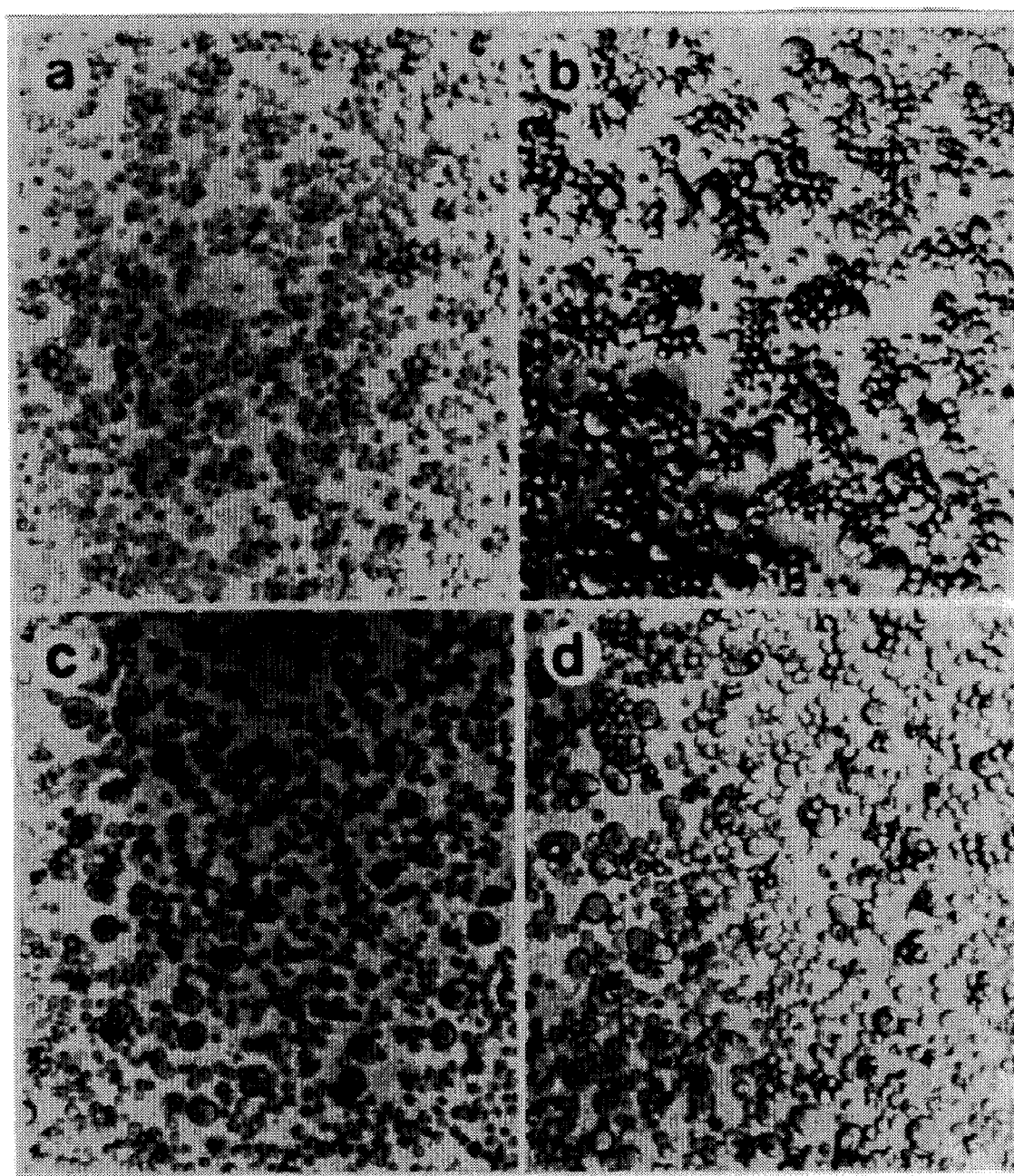
FIG. 1 is a photographic representation of the conditions under which syncytium formation was inhibited in the test performed in Example 1. Picture a is for a negative control where HIV infection-free cells alone were cultured; picture b is for a positive control where infection-free cells and infected cells were mixedly cultured; pictures c and d are for the cases where infection-free cells and infected cells were mixedly cultured in the presence of human urinary trypsin inhibitor (UTI) at concentrations of 1 mM and 100 μM, respectively.

For treating AIDS or preventing the development of AIDS after HIV infection, UTI is preferably administered by the intravenous route, for example by intravenous injection or intravenous drip infusion. Injections for such purposes can be prepared by a per se known method. A preferred intravenous dose for each administration is within the range of 100 to 1,000 mg.

For preventing HIV infection, the use of a UTI-containing preparation suited for topical application to the skin or mucosa portions susceptible to invasion of HIV is recommendable.

Said skin or mucosa portions susceptible to HIV invasion include openings of the human body, such as mouth, throat, nostril, earhole, eyelid, anus, rectum, urethra and vagina, and injured portions, and vicinities thereof.

The infection-inhibiting preparation is generally an external preparation and can be administered in the form of suppository, jelly, cream, cataplasma, ointment, plaster, inunction, liquid, spray, aerosol, powder for external use, etc., as the case may be.

These external preparations can be prepared by a per se known method. For preventing decomposition of UTI in aqueous solution during storage, it is desirable, for example, to dissolve lyophilized UTI in water just prior to use.

The UTI concentration in the infection inhibiting preparation should recommendably be adjusted depending on the dosage form so that a unit dose of 1 to 100 mg can be administered. Compositions can also be in the form of dosage units each containing 10 to 500 mg of human urine trypsin.

When used in accordance with the present invention, human urine trypsin inhibitor (UTI) inhibits the binding of AIDS virus with T cells and thereby prevent the infection with said virus and/or the development of AIDS. UTI also inhibits the proliferation of said virus in the patient's body.

EXAMPLE 1

UTI purified from normal human male-derived urine by Nippon Chemical Research Kabushiki Kaisha was used in this example. Its physico-chemical properties are shown below in Table 1.

TABLE 1

| Test item | Specification | Test result |
|---|---|---|
| Appearance | Colorless to light yellow | Colorless and transparent |
| Identification | | |
| Trypsin activity inhibition | To be confirmed | Confirmed |
| Confirmation of human origin | To be confirmed | Confirmed |
| pH | 5.0–7.5 | 6.54 |
| Purity testing | | |
| Specific activity | ≧2,000 units/mg-p | 2,978 units/mg-p |
| Heavy metals | ≦10 ppm | Requirement met |
| Arsenic | ≦2 ppm | Requirement met |
| Blood group substance | Negative | Negative |
| Blood coagulating substance | Not detectable | Not detectable |
| Urokinase activity | Not detectable | Not detectable |
| Kallikrein activity | ≦0.12 Ku/ml | Requirement met |
| Other proteins | Not detectable | Not detectable |
| Blood pressure lowering substance | Negative | Negative |
| Pyrogen test | JP* | Negative |
| Sterility test | JP* | Negative |
| Safety test | No abnormality | No abnormality |
| HBs antigen test | Negative | Negative |
| Molecular weigh measurement | 67,000 ± 5,000 | Requirement met |
| Assay (potency) | | 140,056 IU/ml |

JP = Japanese Pharmacopeia, 11th edition

The process of purification includes a step of heat treatment in solution form (60° C., 10 hours). Therefore, various viruses had been completely inactivated.

The purity of the UTI used was very high. As shown under some of the purity test items, no proteins other than UTI was detected upon electrophoresis etc.

The above UTI was used in the experiment mentioned below. LAV-1-infected CEM cells (CEM/LAV-1; $2 \times 10^4$ cells) were used as HIV-infected cells and MOLT-4 clone 8 cells ($1 \times 10^5$ cells) as infection-free cells.

When these two kinds of cells were mixedly cultured in a serum-free medium (ASF104) at 37° C. in a 5% $CO_2$ incubator, distinct syncytium formation was found after 18 hours of culture. Addition of UTI to the medium at concentrations of 30 μM, 100 μM, 300 μM and 1 mM resulted in concentration-dependent inhibition of syncytium formation. The pictures shown in FIG. 1 show some of the results obtained.

In FIG. 1, picture a for a negative control where infection-free cells (MOLT-4 clone 8) alone were cultured shows that no syncytium formation occurred. Picture b for a positive control where infection-free cells (MOLT-4 clone 8) and infected cells (CEM/LAV-1) were mixedly cultured shows that distinct syncytium formation took place. Pictures c and d are for the cases where the above-mentioned infection-free cells and infected cells were mixedly cultured with UTI added to the medium at concentrations of 1 mM and 100 μM, respectively, and show that syncytium formation was inhibited in proportion to the UTI concentration.

EXAMPLE 2

A solution (5,000 ml) of purified human urine trypsin inhibitor (150,000 units/ml; protein concentration 54 mg/ml) in 0.025 M phosphate buffer (pH 6.6) containing 0.9% (w/v) sodium chloride was subjected to bacterial filtration, then distributed in 2-ml portions into vials and lyophilized to give preparations for injection.

EXAMPLE 3

Physiological saline (10 ml) was added to 1 g of purified, powdery human urine trypsin inhibitor (lyophilization product). After dissolution, a hydrophilic ointment base was added portionwise to the solution with kneading to give a total weight of 100 g of an ointment.

As detailedly described hereinabove, the present invention provides a composition which can prevent the infection with AIDS virus and the onset of AIDS and thus can be used in the treatment of AIDS patients.

We claim:

1. A method for inhibiting syncytium formation in infection-free cells which come in contact with HIV-infected cells, said method comprising contacting said cells with unit doses of an inhibitory agent comprised of from 10 to 500 mg of human urine trypsin inhibitor.

2. A method for inhibiting the development of the AIDS virus as evidenced by an inhibition of syncytium formation in a subject which comprises administering to said subject unit doses containing 10 to 500 mg of an inhibitory agent comprised of human urine trypsin inhibitor.

* * * * *